(12) United States Patent
O'Lenick et al.

(10) Patent No.: US 7,723,456 B2
(45) Date of Patent: May 25, 2010

(54) CROSSLINKED SILICONE POLYMERS BASED UPON SPIDER ESTERS

(75) Inventors: Kevin O'Lenick, Dacula, GA (US); Anthony J. O'Lenick, Jr., Dacula, GA (US)

(73) Assignee: SurfaTech Corporation, Dacula, GA (US)

( * ) Notice: Subject to any disclaimer, the term of this patent is extended or adjusted under 35 U.S.C. 154(b) by 360 days.

(21) Appl. No.: 12/005,263

(22) Filed: Dec. 27, 2007

(65) Prior Publication Data

US 2009/0171057 A1    Jul. 2, 2009

(51) Int. Cl.
C08G 77/04 (2006.01)
C08G 77/12 (2006.01)
C08L 91/00 (2006.01)

(52) U.S. Cl. .......................... 528/26.5; 528/31; 528/25
(58) Field of Classification Search .................... 528/31
See application file for complete search history.

(56) References Cited

U.S. PATENT DOCUMENTS

| | | | | |
|---|---|---|---|---|
| 5,412,004 | A * | 5/1995 | Tachibana et al. | 524/27 |
| 5,866,666 | A * | 2/1999 | Herzig et al. | 528/25 |
| 6,139,823 | A | 10/2000 | Dreschsler et al. | |
| 6,313,256 | B1 * | 11/2001 | O'Lenick, Jr. | 528/28 |
| 6,388,042 | B1 * | 5/2002 | O'Lenick, Jr. | 528/26 |
| 6,437,162 | B1 * | 8/2002 | O'Lenick, Jr. | 556/445 |
| 2007/0184009 | A1 * | 8/2007 | Rogers et al. | 424/70.31 |
| 2008/0319069 | A1 * | 12/2008 | O'Lenick et al. | 514/549 |
| 2009/0170943 | A1 * | 7/2009 | O'Lenick et al. | 514/552 |
| 2009/0253812 | A1 * | 10/2009 | O'Lenick et al. | 514/786 |

OTHER PUBLICATIONS

Lligadas et al. "Novel Organic-Inorganic Hybrid Materials from Renewable Resources: Hydrosilylation of Fatty Acid Derivatives", Journal of Polymer Science, Part A: Polymer Chemistry, 43, 2005, 6295-6307.*

* cited by examiner

*Primary Examiner*—Randy Gulakowski
*Assistant Examiner*—Robert Loewe

(57) ABSTRACT

The present invention relates to a series of crosslinked silicone polymers that by virtue of the nature of a polar loving spider ester crosslinker, have unique solubility and film forming properties. These include improved tolerance for oily materials and water-soluble materials. These polymers find use in personal care applications like pigmented products. In the personal care arena, solid products that do not experience syneresis are important.

10 Claims, No Drawings

CROSSLINKED SILICONE POLYMERS BASED UPON SPIDER ESTERS

FIELD OF THE INVENTION

The present invention relates to a series of crosslinked silicone polymers that by virtue of the nature of a polar loving spider ester crosslinker have unique solubility and film forming properties. These include improved tolerance for oily materials and water soluble materials. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable. The resins are based upon a technology called spider esters. As will become clear, spider esters are polar loving oil phases that trap polar actives, including sunscreens, antioxidants, alpha an beta hydroxy acids and a variety of other materials. Placing these materials into a silicone backbone results in the ability to make polar loving, film forming materials of interest to the personal care industry as non-penetrating delivery systems.

BACKGROUND OF THE INVENTION

The term silicone resin has been applied both to and misapplied to a variety of materials over time. Silicone resins as used herein refer to a series of products which include at least two silicone backbones that are joined by a "crosslinking group". The number of crosslinking groups that are present as a percentage of the total molecular weight will determine the properties of the resulting polymer.

If there are no crosslinking groups; the polymer can freely rotate and consequently is an oily liquid. If a few crosslinking groups are introduced, the ability to rotate is slightly restricted and the oily material becomes "rubbery". The rubbery material should be referred to as an elastomer. The properties are morel like a rubber band than plastic. As the percentage of crosslinking increases still the molecule becomes rigid. This class of compounds are resins. If you hit the film with a hammer and it shatters it is a resin, if it bounces it is an elastomer and if it squirts out is a silicone fluid.

The difficulty in determining if a product is a fluid an elastomer or resin occurs for products that lie between the classifications. Specifically, when does an elastomer become a resin? While this exact point is of academic interest it does not have any practical significance to the present invention.

There are a number of classes of resin compounds differing in the nature of the crosslinker. One class is the so called "Q resins".

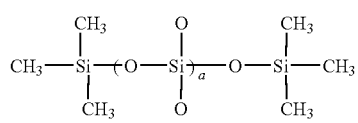

The oxygen that needs another bond connects to another polymer as shown:

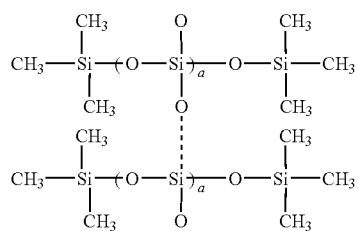

The crosslinking group is —O—. This type of resin is disclosed in U.S. Pat. No. 6,139,823, incorporated herein by reference. This type of material has a group, the so called "Q" group in which a Si has four oxygen atoms attached. In the above case it is the group that is within the "a" subscript. This type of resin is very powdery and is rarely used without a plasticizer. This class of compounds can also dry the skin.

The next class of resin contain alkyl connecting groups.

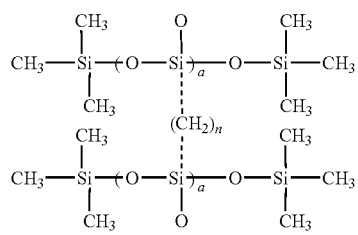

In the case where n=1, acetylene is used as a crosslinking reactant. It is reacted with a silanic hydrogen polymer. As n is increased the reactant is an alpha omega divinyl compound.

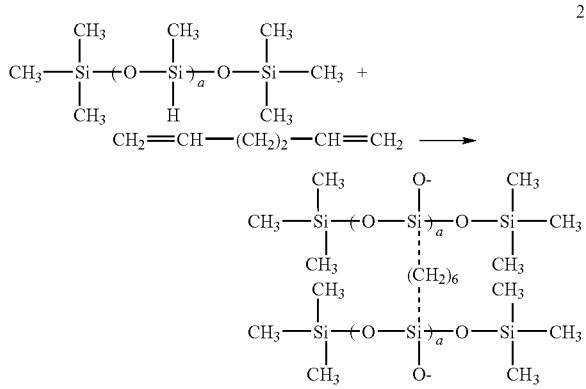

The reaction is called hydrosilylation and provides the linking groups between the molecules. The reaction is generally run in solvent like cyclomethicone (D4, or D5, or hexamethyl disiloxane) or in volatile organic like isododecane. A catalyst generally a platinum one is used to effect the reaction. Chloroplatinic acid or Karnsteadt catalyst are preferred. The resulting material is a viscous liquid that when the solvent evaporates provides a film.

The present invention makes use of novel crosslinking reagents that provide groups that significantly alter the solubility of the resin. This is done by introducing fatty ester linkages, water soluble groups linked with fatty esters and glyceryl esters. Not only does the solubility change, the ability to formulate solid products free from syneresis also occurs. Another unexpected benefit is that the ester moiety provides improved biodegradation of the resin making the resin "more green" and improving consumer acceptability. None of these advantageous are present in the compounds known heretofore.

THE INVENTION

Object of the Invention

It is the object of the present invention to provide a series of silicone polymers that have differing polar loving oil soluble groups. The groups are all reactive with silanic hydrogen to provide a crosslinked product. The crosslinkers all have polar groups rather than alkyl groups.

Another object of the present invention is to provide a series of products suitable for formulation into personal care products providing improved skin feel (i.e. not drying like Q resins) and having improved solubility over alkyl linked polymers.

Other objects of the invention will become clear as one reads the specification attached hereto.

All % given herein are % by weight, all temperatures are °C., all patents and publications referred to herein are incorporated herein by reference in their entirety as appropriate.

SUMMARY OF THE INVENTION

The present invention relates to a series of silicone resins that (a) provide improved water or oil solubility depending upon the specific crosslinker chosen; (b) provide a polar linkage group in the molecules, which in addition to being more polar than alkylene groups, is also more biodegradable; (c) provide products with a low degree of syneresis when placed in lipstick systems.

The compounds of the present invention are made by reacting specific alpha omega multi-vinyl compounds with silicone compounds that contain multiple silanic hydrogen (Si—H) groups. The reaction is conducted in a suitable solvent selected from the group consisting of cyclomethicone (D-4, and D-5, and mixtures thereof) and isoalkanes (iso-dodecane).

DETAILED DESCRIPTION OF THE INVENTION

Resins of the present invention are a class of silicone compounds which are prepared by the reaction of a poly-vinyl compound reacted with a silanic hydrogen containing compound.

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{H}{|}}{\overset{\overset{CH_3}{|}}{Si}})_y-(O-\underset{\underset{R}{|}}{\overset{\overset{CH_3}{|}}{Si}})_z-O-\underset{\underset{CH_3}{|}}{\overset{\overset{CH_3}{|}}{Si}}-CH_3 \; +$$

-continued

Divinyl compound ⟶

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{(CH_2)_2}{|}}{\overset{\overset{CH_3}{|}}{Si}})_y-(O-\underset{\underset{R}{|}}{\overset{\overset{CH_3}{|}}{Si}})_z-O-\underset{\underset{CH_3}{|}}{\overset{\overset{CH_3}{|}}{Si}}-CH_3$$

$$\underset{R'}{|}$$

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{CH_3}{|}}{\overset{\overset{(CH_2)_2}{|}}{Si}})_y-(O-\underset{\underset{R}{|}}{\overset{\overset{CH_3}{|}}{Si}})_z-O-\underset{\underset{CH_3}{|}}{\overset{\overset{CH_3}{|}}{Si}}-CH_3$$

wherein;

x is an integer ranging from 0 to 2000;

y is an integer ranging from 2 to 200;

z is an integer ranging from 0 to 200;

R is selected from the group consisting of H, —(CH$_2$)$_e$—CH$_3$; —(CH$_2$)$_3$—O—(CH$_2$CH$_2$O)$_f$(CH$_2$CH(CH$_3$)O)$_g$(CH$_2$CH$_2$O)$_h$—H;

e is an integer ranging from 6 to 35;

f is an integer ranging from 0 to 20;

g is an integer ranging from 0 to 20;

h is an integer ranging from 0 to 20.

The di-vinyl linking compound is selected from the group consisting of;

(a) glyceryl spider esters conforming to the following structure;

$$H_2C-O-(CH_2CH_2O)_a-(CH_2CH(CH_3)O)_b-C(O)-(CH_2)_8-CH=CH_2$$
$$|$$
$$HC-O-(CH_2CH_2O)_a-(CH_2CH(CH_3)O)_b-C(O)-R^1$$
$$|$$
$$H_2C-O-(CH_2CH_2O)_a-(CH_2CH(CH_3)O)_b-C(O)-(CH_2)_8-CH=CH_2$$

wherein;

a is an integer ranging from 0 to 4;

b is an integer ranging from 0 to 4, with the proviso that a+b ranges from 1 to 4;

R$^1$ is alkyl having 7 to 21 carbon atoms;

(b) glycol spider esters conform to the following structure;

$$(CH_3)_x-C-(CH_2-O-(CH_2CH_2O)_a-(CH_2CH(CH_3)O)_b-C(O)-R^1)_y$$
$$|$$
$$(CH_2OC(O)---(CH_2)_8-CH=CH_2)_z$$

wherein;

a is an integer ranging from 0 to 4;

b is an integer ranging from 0 to 4, with the proviso that a+b ranges from 1 to 5;

R$^1$ is alkyl having 7 to 21 carbon atoms;

z is 2, 3 or 4;
y is 1 or 2;
x+y+z equals 4;
R¹ is alkyl having 7 to 21 carbon atoms; and
(c) sorbitol spider esters conforming to the following structure;

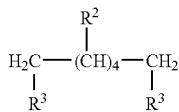

wherein;
a is an integer ranging from 0 to 4;
b is an integer ranging from 0 to 4, with the proviso that a+b ranges from 1 to 5;
R¹ is alkyl having 7 to 21 carbon atoms.

The reactions are typically carried out in a solvent, either volatile silicone (cyclomethicone (D4 or D5 or mixtures thereof) or hydrocarbon solvent like isododecane. A suitable hydrosilylation catalyst like chloroplatinic acid or Karnstedt catalyst are used.

The value of "y" determines the degree of crosslinking and consequently if the product is resinous or elastomeric. Elastomeric materials are compounds that are crosslinked to a lesser extent than resins. They are "rubbery" producing films that are rubber band like. Resins in contrast are not rubbery, but ate hard and because of their higher crosslink density form powders when struck by a hammer.

We have also found that reaction of methyl undecylenate to make the intermediate esters of the present invention provides a finished product that is free of acid value, as opposed to using the fatty acid. Acid value present in the vinyl intermediates causes problems with hydrosilylation.

Cross Linkers

The present invention uses a series so called "spider ester cross linkers". These materials have terminal vinyl groups as the reacting group in making silicones via a process called hydrosilylation. These esters are derived from poly-hydroxy functional compounds sequentially reacted with ethylene oxide or propylene oxide, followed by the reaction of the alkoxylate with fatty acid. The resulting products are called spider esters because they resemble the spider, wherein appendages are alkoxylated esters. The restrictions this orientation imposes on rotation allows for the preparation of polar esters that have little or no water solubility.

The present invention relates to a series of spider ester functionalized silicone polymers. These so-called spider ester silicones of the present invention have (a) a terminal vinyl containing fatty group to provide for reaction with silanic hydrogen, (b) a fatty group connected through a short polyoxyalkylene group to a common linkage group. The so-called linkage group is a consequence of the choice of the proper poly-hydroxy compound. The resulting ester looks like a spider, having a body (linkage group) and multi legs, having a low number of polyoxyalkylene groups present (the leg) and fatty ester groups (the spider's feet). This type of molecule allows groups that are oil soluble (fatty ester "feet"), water attracting (polyoxyalkylene groups (the spider's legs) and a linkage group (poly hydroxy raw material group). The compounds when reacted with silicone form a hybrid polymer that delivers actives from the spider's leg (polyoxyalkylene group), protection from evaporation of moisture (the spider's "fatty feet"), and no surface-active properties, due to the lack of rotation caused by the linkage group.

The present invention is directed to silicone polymer made by the reaction of a silanic hydrogen compound with a polyester conforming to the following structure;
(a) glyceryl spider esters conforming to the following structure;

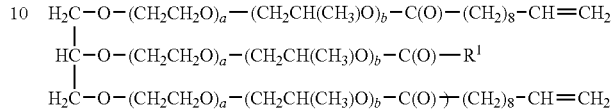

wherein;
a is an integer ranging from 0 to 4;
b is an integer ranging from 0 to 4, with the proviso that a+b ranges from 1 to 4;
R¹ is alkyl having 7 to 21 carbon atoms;
(b) glycol spider esters conform to the following structure;

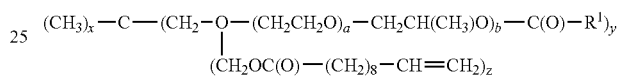

wherein;
a is an integer ranging from 0 to 4;
b is an integer ranging from 0 to 4, with the proviso that a+b ranges from 1 to 5;
R¹ is alkyl having 7 to 21 carbon atoms;
z is 2, 3 or 4;
y is 1 or 2;
x+y+z equals 4:
R¹ is alkyl having 7 to 21 carbon atoms; and
(c) sorbitol spider esters conforming to the following structure;

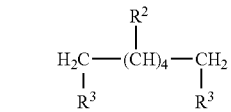

wherein;
R² is —(CH₂CH₂O)ₐ—(CH₂CH(CH₃)O)ᵦ—C(O)—R¹
R³ is —(CH₂CH₂O)ₐ—(CH₂CH(CH₃)O)ᵦ—C(O)—(CH₂)₈—CH=CH₂
a is an integer ranging from 0 to 4;
b is an integer ranging from 0 to 4, with the proviso that a+b ranges from 1 to 5;
R¹ is alkyl having 7 to 21 carbon atoms.

PREFERRED EMBODIMENT

In a preferred embodiment the cross linker is a vinyl terminal glyceryl spider ester.

In a preferred embodiment the glyceryl spider ester b is 0.

In a preferred embodiment the glyceryl spider ester a is 0.

In a preferred embodiment the glyceryl spider ester a is not 0 and b is not 0.

In a preferred embodiment the glyceryl spider ester a is 1 b is 1.

In a preferred embodiment the glyceryl spider ester $R^1$ is alkyl having 7 carbon atoms.

In a preferred embodiment the glyceryl spider ester $R^1$ is alkyl having 9 carbon atoms.

In a preferred embodiment the glyceryl spider ester $R^1$ is alkyl having 11 carbon atoms.

In a preferred embodiment the glyceryl spider ester $R^1$ is alkyl having 13 carbon atoms.

In a preferred embodiment the glyceryl spider ester $R^1$ is alkyl having 19 carbon atoms.

In a preferred embodiment the glyceryl spider ester $R^1$ is alkyl having 21 carbon atoms.

In another preferred embodiment the process is conducted using a glycol spider ester.

In a preferred embodiment the glycol spider ester y is 4.

In a preferred embodiment the glycol spider ester y is 3.

In a preferred embodiment the glycol spider ester y is 4, a is 0 and b is 2.

In a preferred embodiment the glycol spider ester y is 3, a is 0 and b is 2.

In a preferred embodiment the glycol spider ester b is 0.

In a preferred embodiment the glycol spider ester a is 0.

In a preferred embodiment the glycol spider ester a is not 0 and b is not 0.

In a preferred embodiment the glycol spider ester a is 1, b is 1.

In a preferred embodiment the glycol spider ester $R^1$ is alkyl having 7 carbon atoms.

In a preferred embodiment the glycol spider ester $R^1$ is alkyl having 9 carbon atoms.

In a preferred embodiment the glycol spider ester $R^1$ is alkyl having 11 carbon atoms.

In a preferred embodiment the glycol spider ester $R^1$ is alkyl having 13 carbon atoms.

In a preferred embodiment the glycol spider ester $R^1$ is alkyl having 19 carbon atoms.

In a preferred embodiment the glycol spider ester $R^1$ is alkyl having 21 carbon atoms.

In a preferred embodiment the cross linker is a sorbitol spider ester.

In a preferred embodiment the sorbitol spider ester b is 0.

In a preferred embodiment the sorbitol spider ester a is 0.

In a preferred embodiment the sorbitol spider ester a is not 0 and b is not 0.

In a preferred embodiment the sorbitol spider ester a is 1, b is 1.

In a preferred embodiment the sorbitol spider ester $R^1$ is alkyl having 7 carbon atoms.

In a preferred embodiment the sorbitol spider ester $R^1$ is alkyl having 9 carbon atoms.

In a preferred embodiment the sorbitol spider ester $R^1$ is alkyl having 11 carbon atoms.

In a preferred embodiment the sorbitol spider ester $R^1$ is alkyl having 13 carbon atoms.

In a preferred embodiment the sorbitol spider ester $R^1$ is alkyl having 19 carbon atoms.

In a preferred embodiment the sorbitol spider ester $R^1$ is alkyl having 21 carbon atoms.

Raw Material Examples
Glyceryl Alkoxylates

Glyceryl Alkoxylates were prepared by Siltech LLC, of Dacula, Ga. They are made by addition of ethylene oxide, propylene oxide or mixtures thereof to glycerin. They conform to the following structure;

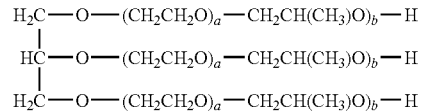

wherein;

a is an integer ranging from 0 to 4;

b is an integer ranging from 0 to 4, with the proviso that a+b ranges from 1 to 4.

Raw Material Examples

| Example | a | b |
|---------|---|---|
| 1 | 0 | 1 |
| 2 | 1 | 1 |
| 3 | 2 | 2 |
| 4 | 1 | 0 |
| 5 | 3 | 1 |
| 6 | 1 | 3 |

Glycol Alkoxylates

Glycol Alkoxylates were prepared by Siltech LLC, of Dacula, Ga. They are made by addition of ethylene oxide, propylene oxide or mixtures thereof to pentaerythritol (y=4), trimethyol propane (y=3). They conform to the following structure;

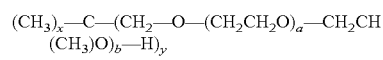

wherein;

a is an integer ranging from 0 to 4;

b is an integer ranging from 0 to 4, with the proviso that a+b ranges from 1 to 5;

$R^1$ is alkyl having 7 to 21 carbon atoms;

y is 4 or 3;

x equals 4−y.

Example 7-12

Pentaerytrhritol Examples (y=4 and x=0)

| Example | a | b |
|---------|---|---|
| 7 | 0 | 1 |
| 8 | 1 | 1 |
| 9 | 2 | 2 |
| 10 | 1 | 0 |
| 11 | 3 | 1 |
| 12 | 1 | 3 |

Example 13-20

Trimethyol Propane Examples (y=e and x=1)

| Example | a | b |
|---------|---|---|
| 13 | 0 | 1 |
| 14 | 1 | 1 |

-continued

| Example | a | b |
| --- | --- | --- |
| 15 | 2 | 2 |
| 16 | 1 | 0 |
| 17 | 3 | 1 |
| 18 | 1 | 3 |

Sorbitol Alkoxylates

Sorbitol is hexane-1,2,3,4,5,6-hexaol. It as a CAS number of 50-70-4

Sorbitol alkoxylates were prepared by Siltech LLC, of Dacula, Ga. They are made by addition of ethylene oxide, propylene oxide or mixtures thereof to sorbitol. They conform to the following structure;

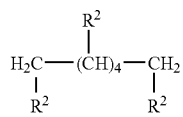

wherein;

$R^2$ is $-(CH_2CH_2O)_a-CH_2CH(CH_3)O)_b-H$ a is an integer ranging from 0 to 4;

b is an integer ranging from 0 to 4, with the proviso that a+b ranges from 1 to 5;

Examples 19-24

| Example | a | b |
| --- | --- | --- |
| 19 | 0 | 1 |
| 20 | 1 | 1 |
| 21 | 2 | 2 |
| 22 | 1 | 0 |
| 23 | 3 | 1 |
| 24 | 1 | 3 |

Fatty Acids

Fatty Acids useful in the practice of the present invention are items of commerce they are available as either single components or mixtures.

Fatty Acids

Alpha Unsaturated Acid

Undecylenic Acid

The acid that is used as the cross linker group is undecylenic acid. It is an item of commerce available from a variety of sources including Caschem in Bayonne N.J. Undecylenic acid conforms to the following structure;

$CH_2=CH-(CH_2)_8-C(O)-OH$

It should become clear that when undecylenic acid is reacted with a hydroxyl containing material, it reacts at the carboxyl group (—C(O)—OH) to form an ester (—C(O)—OR), leaving the terminal vinyl group available for subsequent hydrosilylation.

It is the alpha vinyl group that is reacted with a silanic hydrogen (Si—H) to allow for the formation of a new Si—C bond, placing the spider ester into the silicone backbone.

The incorporation of the spider into the silicone that results in a hybrid material that offers unique properties. It is when there are at least two silanic hydrogen groups in the silicone reactive group and at least two vinyl groups that come from undecylenic acid that a crosslinked system results.

Non Cross Linking Fatty Acids

Fatty acids, which do not contain alpha unsaturation, are also used as raw materials in the preparation of the compounds of the present invention are commercially available from a variety of sources including Procter and Gamble of Cincinnati Ohio. The structures are well known to those skilled in the art.

$R-C(O)-OH$

Saturated

| Example | R Formula | Common Name | Molecular Weight |
| --- | --- | --- | --- |
| 25 | $C_7H_5$ | caprylic | 144 |
| 26 | $C_9H_{19}$ | capric | 172 |
| 27 | $C_{11}H_{23}$ | lauric | 200 |
| 28 | $C_{13}H_{27}$ | myristic | 228 |
| 29 | $C_{14}H_{29}$ | pentadecanoic | 242 |
| 30 | $C_{15}H_{31}$ | palmitic | 256 |
| 31 | $C_{17}H_{35}$ | stearic | 284 |
| 32 | $C_{19}H_{39}$ | arachidinic | 312 |
| 33 | $C_{21}H_{43}$ | behenic | 340 |
| 34 | $C_{26}H_{53}$ | cetrotic | 396 |
| 35 | $C_{33}H_{67}$ | geddic acid | 508 |

Unsaturated Fatty Acids

Internal vinyl groups can be present in the molecule, resulting in improved liquidity. Internal vinyl groups are very slow to react with Si—H in the presence of alpha vinyl groups and represent no problem with the practice of the present invention.

| Example | R Formula | Common Name | Molecular Weight |
| --- | --- | --- | --- |
| 36 | $C_{17}H_{33}$ | oleic | 282 |
| 37 | $C_{17}H_{31}$ | linoleic | 280 |
| 38 | $C_{17}H_{29}$ | linolenic | 278 |
| 39 | $C_{15}H_{29}$ | palmitoleic | 254 |
| 40 | $C_{13}H_{25}$ | myristicoleic | 226 |
| 41 | $C_{21}H_{41}$ | erucic | 338 |

Esterification Reactions

In addition to the ratio of polyoxyalkylene groups to fatty group and the linkage group chosen, it is very important for the practice of the current invention resulting in compounds of the present, the reaction of all of the hydroxyl groups to make esters is very important. The presence of unreacted hydroxyl groups in the compounds of the present invention is undesirable. The compounds of the present invention have very low amount of unreacted hydroxyl groups. Additionally, undecylenic acid is a required raw material for silicone reactivity.

General Procedure

To specified number of grams of undecylenic acid is added the specified number of grams of the specified alkoxylate (Examples 1-24) is added the specified number of grams of the specified fatty acid (Example 25-41). Next add 0.1% by weight, based upon the total number of grams added of both alkoxylate and fatty acid. The reaction mass is heated to 190-200° C. Water is generated as the reaction proceeds. The reaction is followed as the acid value becomes vanishing low. As the reaction proceeds vacuum is applied slowly to keep the water distilling off.

Examples 42-65

| Example | Alkoxylate Example | Alkoxylate Grams | Undecylenic Acid Grams | Fatty Acid Example | Fatty Acid Grams |
|---|---|---|---|---|---|
| 42 | 1 | 89.0 | 96.5 | 25 | 47.5 |
| 43 | 2 | 133.0 | 115.2 | 26 | 56.8 |
| 44 | 3 | 236.0 | 134.0 | 27 | 66.0 |
| 45 | 4 | 74.0 | 152.8 | 28 | 75.2 |
| 46 | 5 | 221.0 | 162.0 | 29 | 80.0 |
| 47 | 6 | 251.0 | 171.0 | 30 | 85.0 |
| 48 | 7 | 87.0 | 142.0 | 31 | 142.0 |
| 49 | 8 | 146.0 | 156.0 | 32 | 156.0 |
| 50 | 9 | 249.0 | 170.0 | 33 | 170.0 |
| 51 | 10 | 87.0 | 198.0 | 34 | 198.0 |
| 52 | 11 | 191.0 | 254.0 | 35 | 254.0 |
| 53 | 12 | 221.0 | 141.0 | 36 | 141.0 |
| 54 | 13 | 102.0 | 187.5 | 37 | 92.5 |
| 55 | 14 | 161.0 | 186.0 | 38 | 92.0 |
| 56 | 15 | 254.0 | 170.0 | 39 | 84.0 |
| 57 | 16 | 92.0 | 151.0 | 40 | 75.0 |
| 58 | 17 | 239.0 | 226.5 | 41 | 111.5 |
| 59 | 18 | 269.0 | 96.0 | 25 | 48.0 |
| 60 | 19 | 89.0 | 115.0 | 26 | 57.0 |
| 61 | 20 | 133.0 | 134.0 | 27 | 66.0 |
| 62 | 21 | 236.0 | 77.5 | 28 | 150.5 |
| 63 | 22 | 74.0 | 82.0 | 29 | 160.1 |
| 64 | 23 | 221.0 | 87.0 | 30 | 169.0 |
| 65 | 24 | 251.0 | 97.0 | 31 | 187.2 |

The reactions are held at temperature until the acid value and hydroxyl becomes vanishing small and the saponification reacted almost theoretical. Products are used without additional purification. They are light in color and low in odor, and are used as reactants with silanic hydrogen materials in the preparation of resins of the present invention.

Silicone Polymers

We have surprisingly and unexpectedly found that by using the spider ester cross linker varying lengths the solubility and film forming properties of the resin can be altered allowing for the preparation of customized films.

The present invention also relates to a series of compounds made by the hydrosilylation reaction of a silanic hydrogen containing silicone conforming to the following structure:

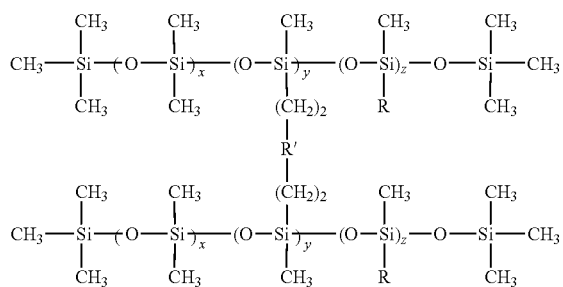

wherein:
x is an integer ranging from 0 to 2000;
y is an integer ranging from 2 to 200;
z is an integer ranging from 0 to 200;
R is selected from the group consisting of H, —$(CH_2)_e$—$CH_3$; —$(CH_2)_3$—O—$(CH_2CH_2O)_f(CH_2CH(CH_3)O)_g$ $(CH_2CH_2O)_h$—H;
e is an integer ranging from 6 to 35;
f is an integer ranging from 0 to 20;
g is an integer ranging from 0 to 20;
h is an integer ranging from 0 to 20;
R' is selected from the group consisting of:
(a) glyceryl spider esters conforming to the following structure:

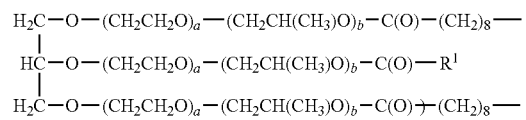

wherein;
a is an integer ranging from 0 to 4;
b is an integer ranging from 0 to 4, with the proviso that a+b ranges from 1 to 4;
$R^1$ is alkyl having 7 to 21 carbon atoms;
(b) glycol spider esters conform to the following structure;

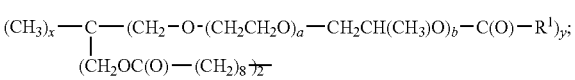

wherein;
a is an integer ranging from 0 to 4;
b is an integer ranging from 0 to 4, with the proviso that a+b ranges from 1 to 5;
$R^1$ is alkyl having 7 to 21 carbon atoms;
z is 2, 3 or 4;
y is 1 or 2;
x+y+z equals 4:
$R^1$ is alkyl having 7 to 21 carbon atoms; and
(c) sorbitol spider esters conforming to the following structure:

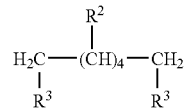

wherein;
$R^2$ is —$(CH_2CH_2O)_a$—$(CH_2CH(CH_3)O)_b$—C(O)—$R^1$
$R^3$ is —$(CH_2CH_2O)_a$—$(CH_2CH(CH_3)O)_b$—C(O)—$(CH_2)_8$—$CH_2$—$CH_2$—
a is an integer ranging from 0 to 4;
b is an integer ranging from 0 to 4, with the proviso that a+b ranges from 1 to 5;
$R^1$ is alkyl having 7 to 21 carbon atoms.

Preferred Embodiments

In a preferred embodiment R' is —$CH_2$—$CH_2$—(O—$CH_2CH_2)_1$—O—$CH_2CH_2$—.
In a preferred embodiment R' is —$CH_2$—$CH_2$—(O—$CH_2CH_2)_2$—O—$CH_2CH_2$—.
In a preferred embodiment R' is —$CH_2$—$CH_2$—O—$(CH_2)_4$—O—$CH_2CH_2$—;
In a preferred embodiment z is 0.
In a preferred embodiment R is H.
In a preferred embodiment R is —$(CH_2)_e$—$CH_3$;
In a preferred embodiment R is —$(CH_2)_3$—O—$(CH_2CH_2O)_f(CH_2CH(CH_3)O)_g(CH_2CH_2O)_h$—

Examples 66-76

Silanic Hydrogen Silicone Compounds

Silanic Hydrogen compounds are items of commerce made by a variety of suppliers, including Siltech Corporation in Toronto Canada. They conform to the following structure:

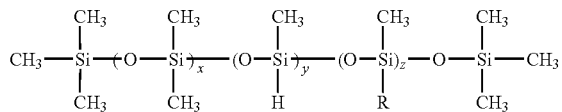

wherein;
x is an integer ranging from 0 to 2000;
y is an integer ranging from 2 to 200;
z is an integer ranging from 0 to 200;
R is selected from the group consisting of H, $-(CH_2)_e-CH_3$; $-(CH_2)_3-O-(CH_2CH_2O)_f(CH_2CH(CH_3)O)_g(CH_2CH_2O)_h-$
e is an integer ranging from 6 to 35;
f is an integer ranging from 0 to 20;
g is an integer ranging from 0 to 20;
h is an integer ranging from 0 to 20.

U.S. Pat. Nos. 3,715,334, and 3,775,452, to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601, Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To the specified number of grams of the specified solvent (Examples 77-79) is added the specified number of grams of the specified silanic hydrogen compound (Example 66-77). The mass is mixed well. To that mixture is added the specified number of grams of the specified vinyl crosslinker compound (Example 42-65). The reaction mass is mixed well until homogeneous. To that mixture is added 0.1% Karstedt catalyst, which is commercially available from Geleste. The agitation is stopped and the reaction begins. The reaction mass will thicken over 4, hours. Once the maximum viscosity is

| Example | X | Y | Z | R | F | g | h | e |
|---|---|---|---|---|---|---|---|---|
| 66 | 0 | 2 | 0 | None | None | None | None | None |
| 67 | 10 | 5 | 20 | $-(CH_2)_eCH_3$ | None | None | None | 6 |
| 68 | 15 | 20 | 15 | $-(CH_2)_3O(EO)_f(PO)_g(EO)_hH$ | 0 | 0 | 0 | None |
| 69 | 25 | 50 | 9 | $-H$ | None | None | None | None |
| 70 | 50 | 25 | 50 | $-(CH_2)_3O(EO)_f(PO)_g(EO)_hH$ | 10 | 5 | 10 | None |
| 71 | 75 | 15 | 0 | None | None | None | None | None |
| 72 | 100 | 28 | 5 | $-H$ | None | None | None | None |
| 73 | 5 | 5 | 15 | $-(CH_2)_3O(EO)_f(PO)_g(EO)_hH$ | 20 | 20 | 20 | None |
| 74 | 10 | 150 | 10 | $-(CH_2)_eCH_3$ | None | None | None | 35 |
| 75 | 6 | 100 | 200 | $-(CH_2)_3O(EO)_f(PO)_g(EO)_hH$ | 0 | 10 | 0 | None |
| 76 | 2000 | 200 | 0 | None | None | None | None | None |

Hydrosilylation Compounds of the Present invention

Examples 78-80

Hydrosilylation Solvents

The hydrosilylation reactions are advantageously run in a volatile solvent, which can later be distilled off is desired. It is also a practice to sell the products in solvent.

| Example | Description |
|---|---|
| 77 | isododecane |
| 78 | cyclomethicone |
| 79 | isodecane |

Hydrosilylation

Hydrosilylation is a process that reacts terminal vinyl compounds with silanic hydrogen to obtain a Si—C bond. References to this reaction, incorporated herein by reference, include:

reached the reaction is considered complete. The solvent may be distilled off or the product may be sold as prepared without additional purification.

Examples 80-103

| Example | Vinyl compound Example | Grams | Silanic Hydrogen Example | Grams | Solvent Example | Grams |
|---|---|---|---|---|---|---|
| 80 | 42 | 3.5 | 66 | 15.4 | 77 | 781.8 |
| 81 | 43 | 3.6 | 67 | 91.4 | 78 | 1417.0 |
| 82 | 44 | 5.2 | 68 | 19.2 | 79 | 439.3 |
| 83 | 45 | 3.5 | 60 | 12.6 | 77 | 184.7 |
| 84 | 46 | 3.8 | 70 | 578.6 | 78 | 6361.0 |
| 85 | 47 | 5.2 | 71 | 763.6 | 79 | 8063.0 |
| 86 | 48 | 3.5 | 72 | 745.1 | 77 | 8030.1 |
| 87 | 49 | 5.2 | 73 | 65.7 | 78 | 1904.0 |
| 88 | 50 | 3.6 | 74 | 15.4 | 79 | 781.8 |
| 89 | 51 | 3.8 | 75 | 91.4 | 77 | 1417.0 |
| 90 | 52 | 5.2 | 76 | 19.2 | 78 | 439.3 |
| 91 | 52 | 3.5 | 66 | 15.4 | 79 | 781.8 |
| 92 | 54 | 3.9 | 67 | 91.4 | 77 | 1417.0 |
| 93 | 55 | 5.1 | 68 | 19.2 | 78 | 439.3 |
| 94 | 56 | 3.6 | 69 | 12.6 | 79 | 184.7 |

-continued

| Ex- | Vinyl compound | | Silanic Hydrogen | | Solvent | |
|---|---|---|---|---|---|---|
| ample | Example | Grams | Example | Grams | Example | Grams |
| 95 | 57 | 3.8 | 70 | 578.6 | 77 | 6361.0 |
| 96 | 58 | 5.2 | 71 | 763.6 | 78 | 8063.0 |
| 97 | 59 | 3.6 | 72 | 745.1 | 79 | 8030.1 |
| 98 | 60 | 5.2 | 73 | 65.7 | 77 | 1904.0 |
| 99 | 61 | 3.5 | 74 | 15.4 | 78 | 781.8 |
| 100 | 62 | 3.8 | 75 | 91.4 | 79 | 1417.0 |
| 101 | 63 | 5.2 | 76 | 19.2 | 77 | 439.3 |
| 102 | 64 | 3.8 | 67 | 91.4 | 78 | 1417.0 |
| 103 | 65 | 5.2 | 68 | 19.2 | 79 | 439.3 |

The key to understanding the functionality of the resin of the present invention is an appreciation that polar materials and be incorporated into a film forming material and deposited on the skin. This results in a delivery of actives to the skin from within the spider ester, which is in turn trapped in the film.

As is clear the ability to change the linking group within a resin results in a variety of changes in the ability to make personal care products that have desirable properties. This relates to the ability to keep oil soluble materials, water soluble materials and silicone soluble materials in the same formulation, providing a cosmetically acceptable product. The products of the present invention allow for greater formulation latitude and also allow for the introduction of new products hereto for not attainable.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A silicone polymer made by the hydrosilylation reaction of a silanic hydrogen containing silicone conforming to the following structure:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{H}{|}}{\overset{\overset{CH_3}{|}}{Si}})_y-(O-\underset{\underset{R}{|}}{\overset{\overset{CH_3}{|}}{Si}})_z-O-\underset{\underset{CH_3}{|}}{\overset{\overset{CH_3}{|}}{Si}}-CH_3$$

wherein;
x is an integer ranging from 0 to 2000;
y is an integer ranging from 2 to 200;
z is an integer ranging from 0 to 200;
R is selected from the group consisting of H, $-(CH_2)_e-CH_3$; $-(CH_2)_3-O-(CH_2CH_2O)_f(CH_2CH(CH_3)O)_g(CH_2CH_2O)_h-H$;
e is an integer ranging from 6 to 35;
f is an integer ranging from 0 to 20;
g is an integer ranging from 0 to 20;
h is an integer ranging from 0 to 20;
and a spider ester cross linker selected from the group consisting of;

(a) glyceryl spider esters conforming to the following structure;

$$H_2C-O-(CH_2CH_2O)_a-(CH_2CH(CH_3)O)_b-C(O)-(CH_2)_8-CH=CH_2$$
$$HC-O-(CH_2CH_2O)_a-(CH_2CH(CH_3)O)_b-C(O)-R^1$$
$$H_2C-O-(CH_2CH_2O)_a-(CH_2CH(CH_3)O)_b-C(O)+(CH_2)_8-CH=CH_2$$

wherein;
a is an integer ranging from 0 to 4;
b is an integer ranging from 0 to 4, with the proviso that a+b ranges from 1 to 4;
$R^1$ is alkyl having 7 to 21 carbon atoms;

(b) glycol spider esters conform to the following structure;

$$(CH_3)_x-\underset{\underset{(CH_2OC(O)-(CH_2)_8-CH=CH_2)_z}{|}}{C}-(CH_2-O-(CH_2CH_2O)_a-(CH_2CH(CH_3)O)_b-C(O)-R^1)_y$$

wherein;
a is an integer ranging from 0 to 4;
b is an integer ranging from 0 to 4, with the proviso that a+b ranges from 1 to 5;
$R^1$ is alkyl having 7 to 21 carbon atoms;
z is 2, 3 or 4;
y is 1 or 2;
x+y+z equals 4;
$R^1$ is alkyl having 7 to 21 carbon atoms;
and (c) sorbitol spider esters conforming to the following structure;

$$H_2C-\underset{\underset{R^3}{|}}{(CH)_4}-\underset{\underset{R^3}{|}}{\overset{\overset{R^2}{|}}{CH_2}}$$

wherein;
$R^2$ is $-(CH_2CH_2O)_a-(CH_2CH(CH_3)O)_b-C(O)-R^1$
$R^3$ is $-(CH_2CH_2O)_a-(CH_2CH(CH_3)O)_b-C(O)-(CH_2)_8-CH=CH_2$
a is an integer ranging from 0 to 4;
b is an integer ranging from 0 to 4, with the proviso that a+b ranges from 1 to 5;
$R^1$ is alkyl having 7 to 21 carbon atoms;
in the presence of a suitable hydrosilylation catalyst;
in a suitable volatile solvent selected from the group consisting of cyclomethicone, hexamethyldisiloxane and isoparaffin.

2. A silicone polymer of claim 1 wherein z is 0.

3. A silicone polymer of claim 1 wherein R is H.

4. A silicone polymer of claim 1 wherein R is $-(CH_2)_e-CH_3$.

5. A silicone polymer of claim 1 wherein R is $-(CH_2)_3-O-(CH_2CH_2O)_f(CH_2CH(CH_3)O)_g(CH_2CH_2O)_h-H$.

6. A silicone polymer conforming to the following structure:

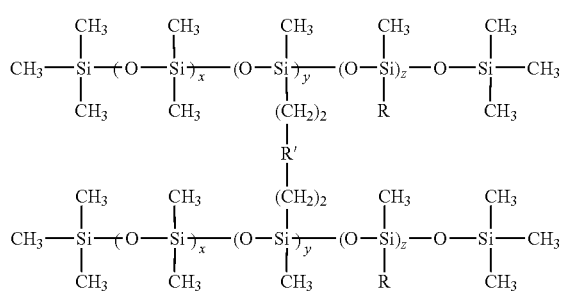

wherein:
x is an integer ranging from 0 to 2000;
y is an integer ranging from 2 to 200;
z is an integer ranging from 0 to 200;
R is selected from the group consisting H, —$(CH_2)_e$—$CH_3$; —$(CH_2)_3$—O—$(CH_2CH_2O)_f$$(CH_2CH(CH_3)O)_g$$(CH_2CH_2O)_h$—H
e is an integer ranging from 6 to 35;
f is an integer ranging from 0 to 20;
g is an integer ranging from 0 to 20;
h is an integer ranging from 0 to 20;
R' is selected from the group consisting of
(a) glyceryl spider esters conforming to the following structure;

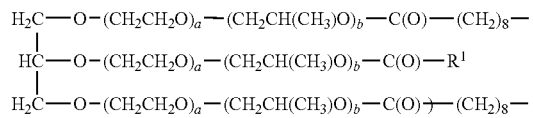

wherein;
a is an integer ranging from 0 to 4;
b is an integer ranging from 0 to 4, with the proviso that a+b ranges from 1 to 4;
$R^1$ is alkyl having 7 to 21 carbon atoms;

(b) glycol spider esters conform to the following structure;

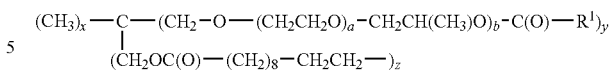

wherein;
a is an integer ranging from 0 to 4;
b is an integer ranging from 0 to 4, with the proviso that a+b ranges from 1 to 5;
$R^1$ is alkyl having 7 to 21 carbon atoms;
z is 2, 3 or 4;
y is 1 or 2;
x+y+z equals 4;
$R^1$ is alkyl having 7 to 21 carbon atoms;
and
(c) sorbitol spider esters conforming to the following structure;

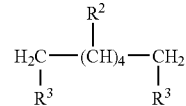

wherein;
$R^2$ is —$(CH_2CH_2O)_a$—$(CH_2CH(CH_3)O)_b$—C(O)—$R^1$
$R^3$ is —$(CH_2CH_2O)_a$—$(CH_2CH(CH_3)O)_b$—C(O)—$(CH_2)_8$—$CH_2CH_2$—
a is an integer ranging from 0 to 4;
b is an integer ranging from 0 to 4, with the proviso that a+b ranges from 1 to 5;
$R^1$ is alkyl having 7 to 21 carbon atoms.

7. A silicone polymer of claim 6 wherein z is 0.

8. A silicone polymer of claim 6 wherein R is H.

9. A silicone polymer of claim 6 wherein R is —$(CH_2)_o$—$CH_3$.

10. A silicone polymer of claim 6 wherein R is —$(CH_2)_3$—O—$(CH_2CH_2O)_f$$(CH_2CH(CH_3)O)_g$$(CH_2CH_2O)_h$—H.

* * * * *